United States Patent [19]

Putman

[11] Patent Number: 5,184,601
[45] Date of Patent: Feb. 9, 1993

[54] ENDOSCOPE STABILIZER

[76] Inventor: John M. Putman, 3707 Gaston Ave., Suite 410, Dallas, Tex. 75246

[21] Appl. No.: 740,413

[22] Filed: Aug. 5, 1991

[51] Int. Cl.[5] .............................................. A61B 1/00
[52] U.S. Cl. ........................................ 128/4; 901/17; 128/6; 312/209
[58] Field of Search ................................ 128/4, 6, 20; 901/15–17, 23; 433/49, 77, 105, 106; 312/209; 606/45, 46

[56] References Cited

U.S. PATENT DOCUMENTS

| | | | |
|---|---|---|---|
| 3,043,448 | 7/1962 | Melton | 901/17 X |
| 3,575,301 | 4/1971 | Panissidi | 901/16 X |
| 4,229,136 | 10/1980 | Panissidi | 901/16 X |
| 4,510,926 | 4/1985 | Inaba | 128/20 |
| 4,573,452 | 3/1986 | Greenberg | 128/20 |
| 4,593,681 | 6/1986 | Soni | 128/4 |
| 4,601,284 | 7/1986 | Arakawa et al. | 128/6 |
| 4,854,301 | 8/1989 | Nakajima | 128/4 |
| 4,867,404 | 9/1969 | Harrington et al. | 248/231.4 |

OTHER PUBLICATIONS

Brochure, "Elmed Endoscopic Fixation Device", Elmed Incorporated.

Primary Examiner—Theatrice Brown
Assistant Examiner—J. Doyle
Attorney, Agent, or Firm—Dennis T. Griggs

[57] ABSTRACT

A portable console includes a universal positioning arm for holding a surgical instrument such as an endoscope during a surgical procedure. Coarse adjustment of instrument elevation above an operating table is provided by a reversible drive motor which extends and retracts an upright support shaft from which the instrument is supported. Coarse adjustment of instrument X-Y position within the sterile zone above an operating table is provided by an articulate arm which is rotatably coupled to the upright support shaft. Fine adjustment of instrument position across the sterile zone is provided by a reversible drive motor which extends and retracts the instrument along the longitudinal axis of the support arm. Fine adjustment of instrument elevation is provided by a reversible drive motor which lifts and lowers the distal end of the support arm. The insertion orientation of the instrument is adjustable by a rotatable coupling. Coarse positioning is performed by actuation of console and arm-mounted switches, and fine positioning is performed by foot pressure applied to floor switches by the operating surgeon.

10 Claims, 7 Drawing Sheets

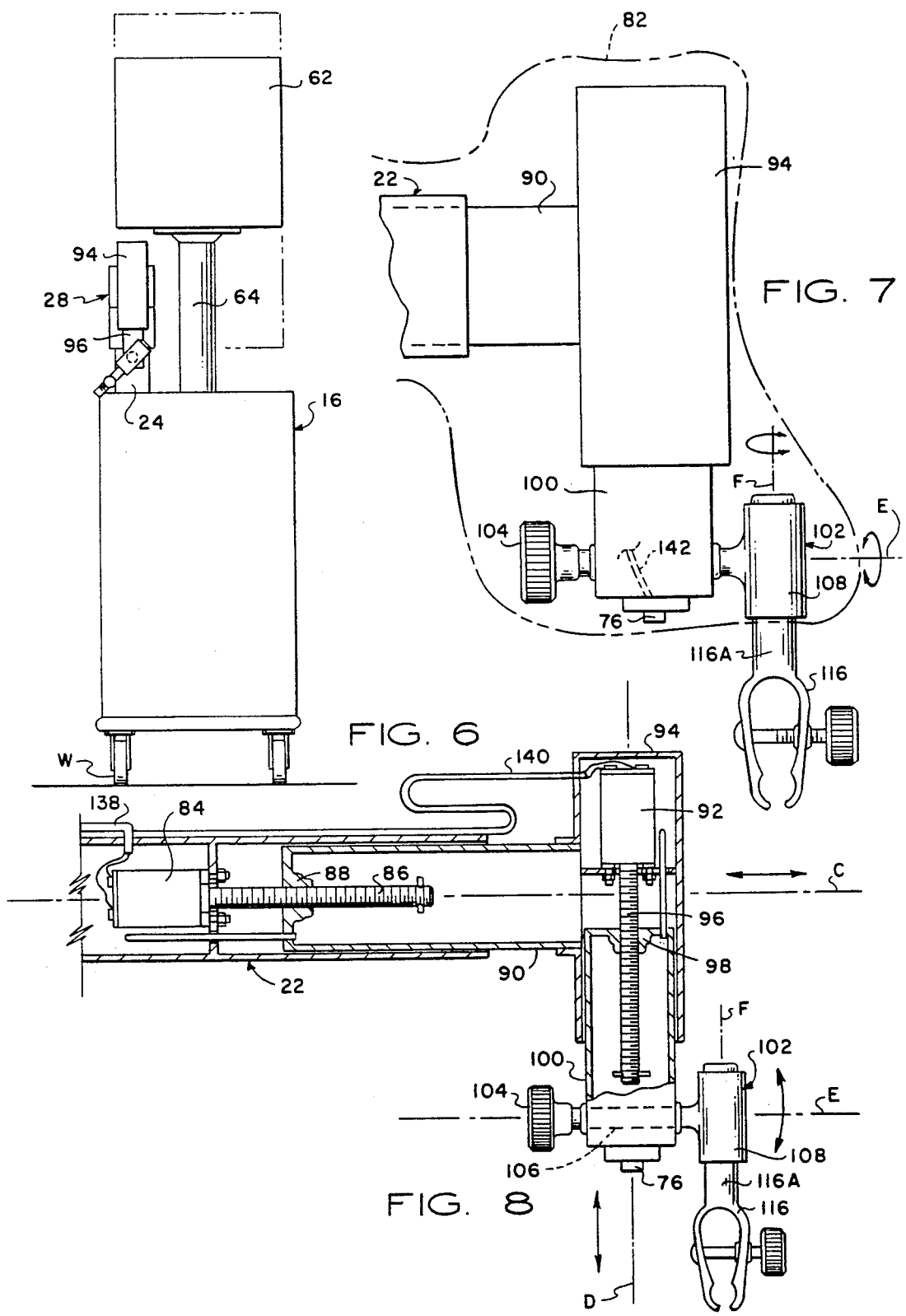

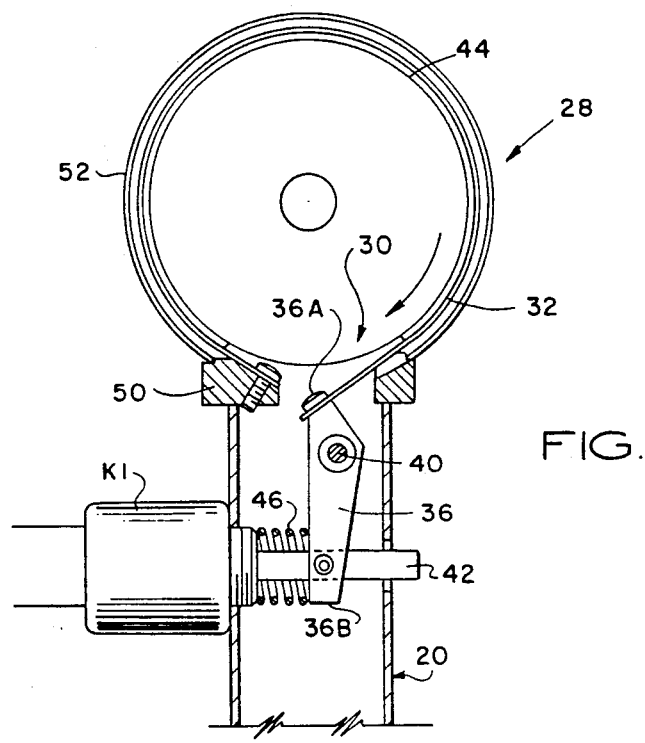
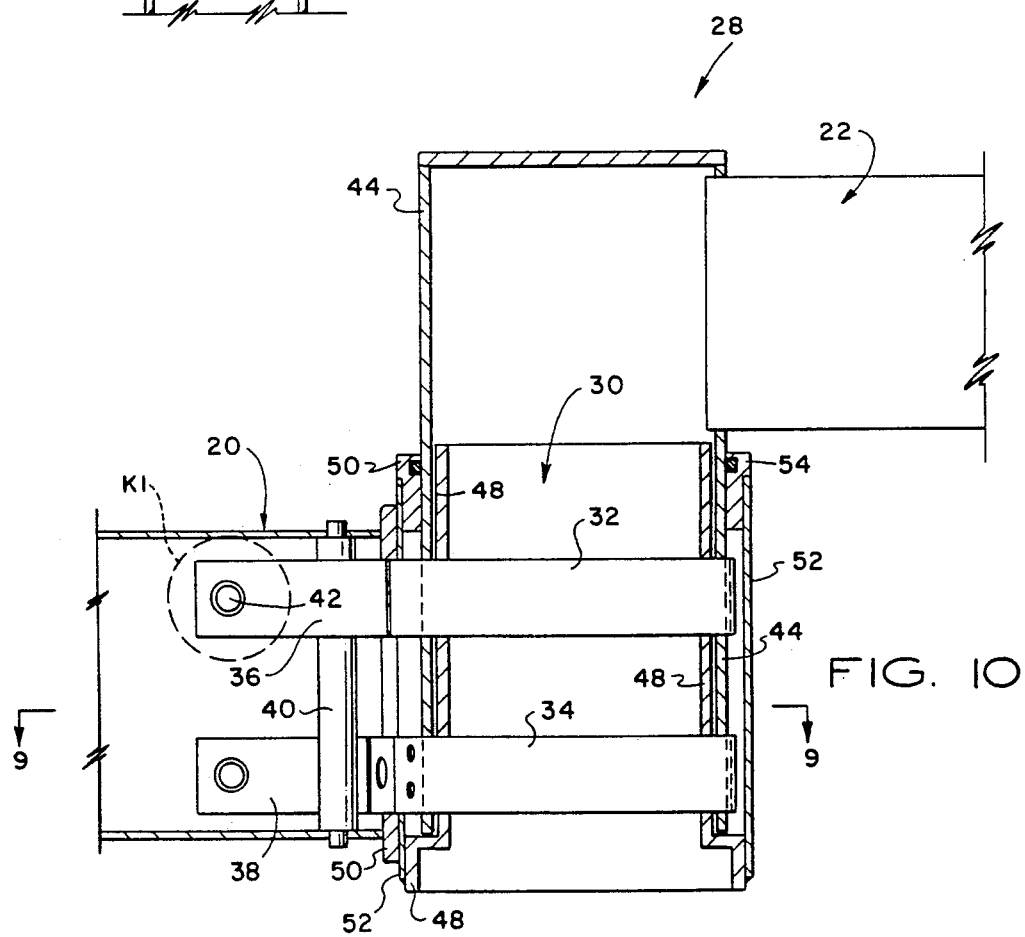

ENDOSCOPE STABILIZER

FIELD OF THE INVENTION

This invention relates generally to the art of universal positioning devices, and in particular to a portable console assembly for selectively positioning and stabilizing an instrument such as an endoscope during a surgical procedure.

BACKGROUND OF THE INVENTION

In the performance of surgery and related procedures, sterile operating conditions are maintained by a surgical drape which covers the patient and the operating table. The surgical procedure is performed through a slit or preformed fenestration which is aligned with a desired surgical site. It is sometimes necessary to support and stabilize an instrument such as endoscope in an elevated position above the patient for long periods of time, with a portion of the instrument being inserted into the patient's abdominal cavity. An endoscope is a slender viewing tube which may be rigid or flexible, and which includes an optical lens system and a light source. The purpose of the endoscope instrument is to provide visual access into a body cavity, for example, the abdominal cavity, the knee, shoulder, bladder, uterus and bowel. A laparoscope is a type of endoscope which includes a rigid viewing tube for insertion through the abdominal wall.

It is necessary to vary the position of the instrument from time to time according to the needs of the surgical procedure. During a laparoscopic cholecystectomy (gall bladder removal), for example, an endoscope is inserted into the upper abdominal cavity which is inflated and pressurized with carbon dioxide by an insufflating machine. The endoscope is guided through a trocar sheath which serves as an interface port through the abdominal wall. By sliding the endoscope up and down the port, or rotating it in the desired direction, a view of the internal organs can be obtained by a video camera which is attached to the endoscope, and with the image being displayed on a video monitor.

The video camera also records the movement of other surgical instruments, for example, a grasper, a hook, a spatula, forceps and dissector, which are guided into and out of the abdominal cavity through one or more secondary surgical trocar sheaths. When the distal tip of the instrument appears on the video monitor, the surgeon guides it into place and controls its action and movement as displayed on the video monitor. It is usually necessary to re-position the endoscope from time to time to view the operative site so that the surgical instruments are positioned appropriately within the cavity to expose the organ or internal tissue for inspection, repair, dissection or excision.

The success of the laparoscopy procedure depends in part on the surgeon's ability to gauge spatial relationships as viewed on the video monitor, and to be able to easily adjust or reposition the endoscope as the procedure progresses. During gall bladder removal, for example, it may be necessary to re-position the endoscope and hold it in a desired orientation as the gall bladder duct is sealed by a surgical clip. Additionally, it may be necessary to re-position the endoscope while using an electrocautery instrument to excise the gall bladder from the underside of the liver. After the gall bladder organ has been severed, it is removed through an exit port. It is then necessary to reposition the endoscope to an upper midline port so that the surgeon can correctly position and operate a grasper instrument through a secondary trocar port.

Examples of procedures which may be performed or assisted by endoscopy include the following:

| Diagnostic | Tubal Sterilization | Ablation Endometriosis |
|---|---|---|
| Ovarian Biopsy | Ovarian Cyst Aspiration | Ovarian Cystectomy |
| Ovarian Endocoagulation | Oophorectomy | Laser Uterine Nerve Ablation |
| Presacral Neurectomy | Salpingoplasty | Salpingostomy |
| Salpingectomy | Tubal Reanastomosis | Myomectomy |
| Pelvic Abscess | Removal of foreign body (IUD) | In Vitro Fertilization |
| Hysterectomy | Ovarian Torsion | Multiple Peritoneal Biopsies |
| Omentectomy | Lymphadenectomy | Lysis Bowel Adhesions |
| Appendectomy | Cholecystectomy | Colectomy |
| Hernia Repair | Gonadectomy | Nephrectomy |

Other procedures which may be assisted by endoscopy include orthopedic knee surgery, orthopedic shoulder surgery, urological procedures, bowel procedures, and other gynecological procedures.

DESCRIPTION OF THE PRIOR ART

In the performance of surgical procedures within the abdominal cavity in which an endoscope instrument is utilized, the endoscope instrument is inserted into the abdominal cavity and must be supported and held in a fixed position during the procedure, and its position must be adjusted from time to time. Once the precise anatomy-viewing position is established, it must be securely maintained. Otherwise, the physician's view will be interrupted, prolonging the procedure, with loss of visual contact at a critical moment during the operation. Moreover, the laparoscope instrument might, due to slippage, exert pressure on tissues and soft organs, such as the liver, pancreas and intestines.

In some cases, operating room personnel manually hold the endoscope instrument in the desired position, and move it about according to the surgeon's instructions. The use of operating room personnel to support such instruments during an extended surgical procedure is unsatisfactory in that the assistant may be unable to maintain stability because of muscle fatigue, and find it necessary to change position at some critical or otherwise inconvenient time.

Support devices which are mountable onto an operating table have been used for holding surgical instruments such as endoscopes and retractors. Such equipment may be clamped onto the operating table and are moved about from time to time as required by the surgical procedure. However, such devices may restrict access to the surgical site and have limited maneuverability.

Operating tables are provided with narrow side rails on which surgical support equipment can be attached. However, because the side rails are closely located to the sterile operating field, certain instrument support positions are difficult to achieve with such rail-mounted support apparatus. Generally, it is desirable to support surgical instruments in offset relation with respect to the operating table and side rails to allow a wide range of support positions.

Moreover, some rail-mounted positioning equipment must be manually released from time to time to re-position instruments which are suspended above the sterile operating zone. It will be appreciated that in surgical procedures, time is of the essence, and delays associated with adjustment of support equipment prolong the procedure. Additionally, the presence of surgical support equipment within the sterile operating zone limits the surgeon's access to the patient during the procedure. Thus it is generally desirable to limit the number of surgical support devices in and about the sterile zone so that the operating surgeon and his attendants will have clear and unrestricted access to the patient, and also will have a clear and unrestricted view of a video monitor.

During certain procedures, it may be desirable to impose or change a biasing force on the surgical instrument to stabilize its position within the abdominal cavity. It is awkward or impossible in some instances to apply such bias forces through instruments or apparatus which are mounted directly onto the side rail. Thus, it is desirable to offset such equipment both laterally and vertically in the regions immediately surrounding the sterile zone of the operating table.

OBJECTS OF THE INVENTION

Accordingly, there is a specific need for surgical instrument support apparatus which may be set up on a portable console outside of the sterile field for supporting a surgical instrument, such as an endoscope, at a desired viewing position and orientation within a body cavity, with the position of the instrument supporting apparatus being stable when set, and being easily and quickly adjustable to different support positions as desired.

One object of the present invention is to provide a portable console having an articulated arm which can be extended and moved about within the sterile zone overlying an operating table, thereby providing stable support for a surgical instrument such as an endoscope at an unlimited number of internal viewing locations.

A related object of the present invention is to provide a stabilizer console as described, in which the articulated arm can be raised and lowered as desired within the sterile zone overlying an operating table, thereby providing a wide range of instrument orientations and patient clearance.

Yet another object of the present invention is to provide a portable console having an articulated support arm in which the console and support arm can be quickly set up adjacent to an operating table, with the articulated arm being quickly adjustable to a desired orientation relative to the patient.

Another object of the present invention is to provide a portable console having an articulated arm as described with the position of the articulated arm being subject to coarse control adjustment during initial set up by an attendant, and subject to fine control adjustment by a surgeon during a surgical procedure.

A related object of the present invention is to provide a portable console of the character described in which the fine control adjustment is carried out by the surgeon actuating a foot switch assembly during the course of a surgical procedure.

Still another object of the present invention is to provide a portable console of the type described in which remotely operable means are provided for locking and releasing the joints of the articulated arm so that it can be quickly re-positioned by the surgeon during the course of a surgical procedure.

A related object of the present invention is to provide a portable stabilizer console having an articulated arm of the type described in which deflection of the articulated arm is minimized.

Yet another object of the present invention is to provide a portable console of the type described which includes one or more internal compartments for storage of accessories such as video recording equipment, video camera, endoscope equipment, video display equipment, electrical power cable, foot switch and foot switch connecting cable.

SUMMARY OF THE INVENTION

The present invention provides a portable console having a universal positioning arm for holding and stabilizing a surgical instrument such as an endoscope during a surgical procedure, which is quickly and easily adjustable to a wide range of stable support positions.

The console-mounted positioning apparatus of the present invention includes an articulated support arm, including means for coarse position control and fine position control of the height and orientation of a surgical instrument within a sterile zone above or about a standard surgical operating table. In particular, the apparatus of the present invention includes a console on which a vertical support shaft is mounted for adjustable movement in elevation. An articulated arm for holding and stabilizing an instrument such as an endoscope is rotatably coupled to the vertical support shaft. The console includes a height adjustment drive motor coupled to the vertical support shaft, a releasable brake, and positioning drive motors which are controlled by a foot switch for accurately positioning the distal end of a surgical instrument within the abdominal cavity of a patient who is undergoing surgery, for example, gall bladder removal in the upper abdominal cavity, or gynecological procedures in the lower pelvic cavity. The stabilizing arm has two sections which are independently rotatable with respect to each other to provide a wide range of positioning control of the surgical instrument within the sterile zone. The joints of the articulated arm are coupled by band brakes which are lockable and releasable upon application of an electrical control signal from a console switch, or upon application of an electrical control signal from an override switch attached to the articulated arm.

The features and advantages of the present invention will be further appreciated by those skilled in the art upon reading the detailed description which follows with reference to the drawings.

BRIEF DESCRIPTION OF THE DRAWINGS

FIG. 6 is a left side elevational view thereof;

FIG. 7 is a side elevational view of an endoscope coupler;

FIG. 8 is a view similar to FIG. 6, partly in section, showing a positioning drive motor assembly;

FIG. 9 is a sectional view of a band brake assembly taken along the line 9—9 of FIG. 10;

FIG. 10 is a sectional view of a band brake assembly; and,

DETAILED DESCRIPTION OF THE PREFERRED EMBODIMENT

Figure 1:
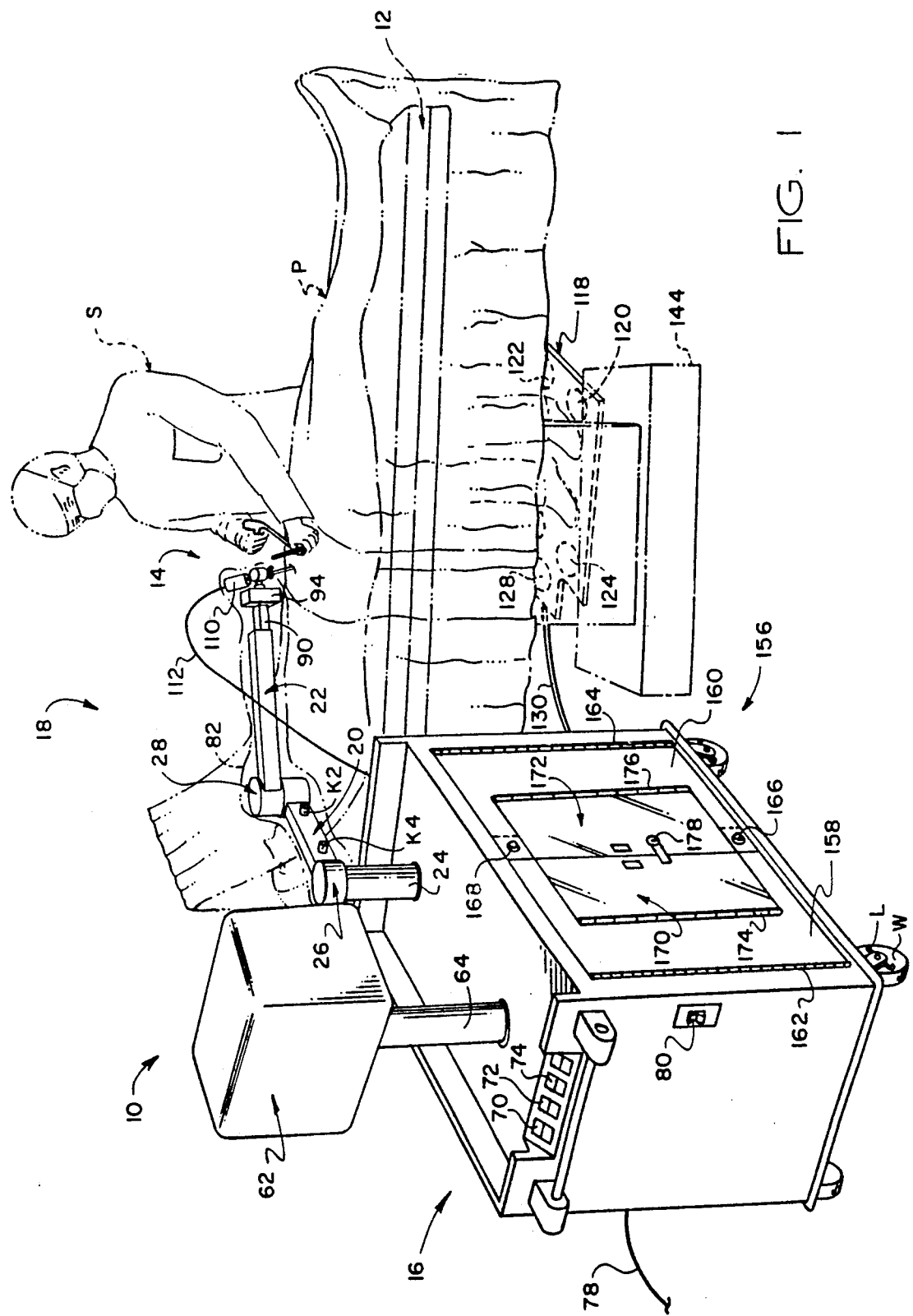
FIG. 1 is a perspective view of the portable console positioning apparatus of the present invention shown set up adjacent to a surgical operating table.

In the description which follows, like parts are indicated throughout the specification and drawings with the same reference numerals, respectively. The drawings are not necessarily to scale, and the proportions of certain parts have been exaggerated to better illustrate certain structural details.

The positioning apparatus 10 of the present invention is particularly well suited for use in combination with a conventional surgical operating table 12 during the performance of abdominal, pelvic, joint, bladder, bowel and uterine surgery.

Figure 2:
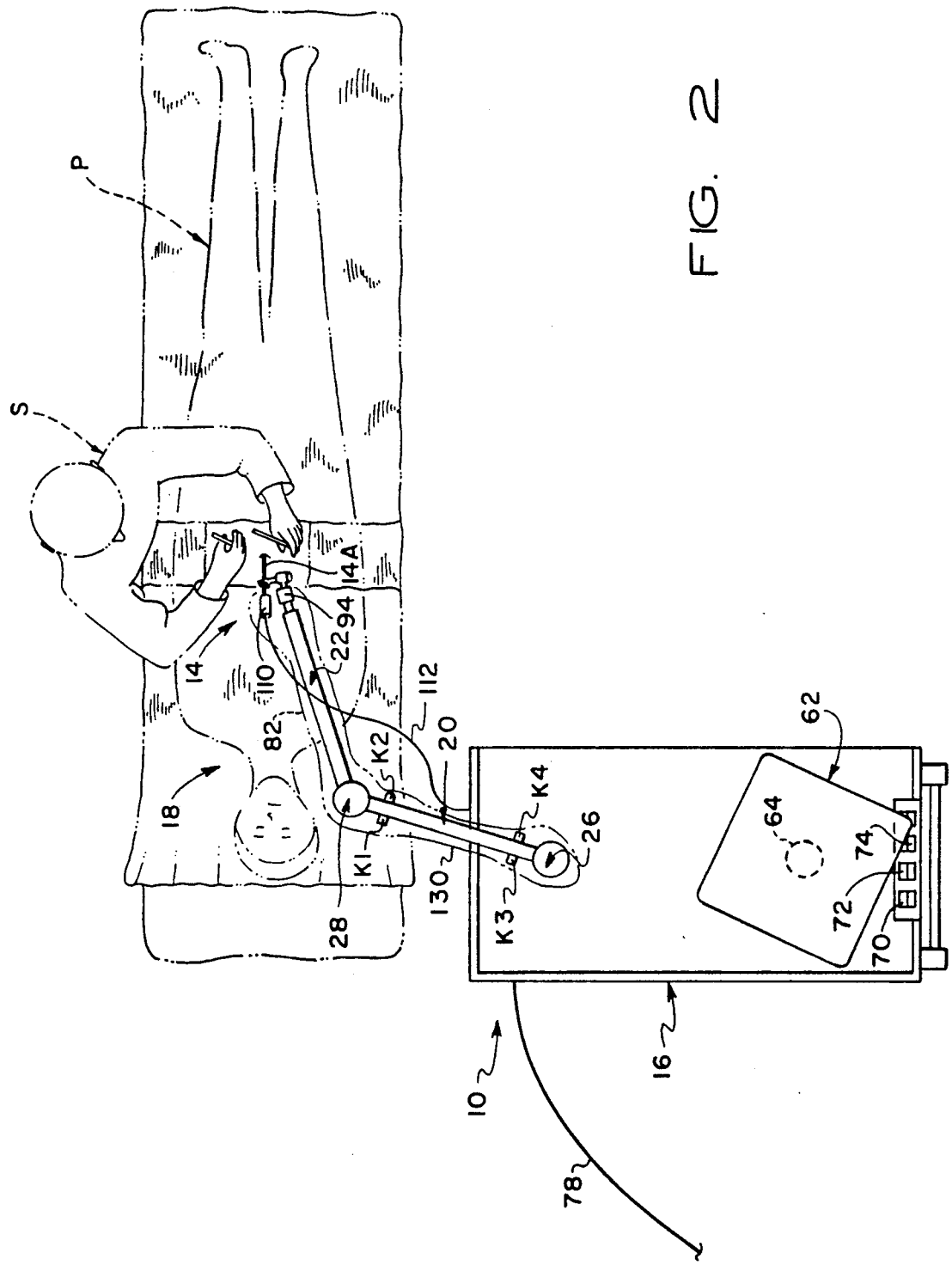
FIG. 2 is a top plan view of the portable console positioning apparatus and surgical operating table as shown in FIG. 1.

Referring now to FIG. 1 and 2, the surgical instrument support apparatus 10 of the present invention is shown set up adjacent to an operating table 12 for positioning endoscope 14 during a surgical procedure in the abdominal cavity of a patient P. Stable support is provided by a portable console 16 which is equipped with lockable wheels W for permitting rolling movement of the console from one station to another. The portable console 16 is parked adjacent to the operating table 12, and is positioned substantially at a right angle with respect to the operating table to provide standing room for attendants who assist the surgeon S. After the portable console 16 has been positioned correctly, its wheels W are locked by depressing the wheel lock arms L, and the surgical instrument support apparatus 10 is made ready by an attendant.

The endoscope 14 is supported by an articulated arm assembly 18 which includes a first (proximal) support arm section 20 and a second (distal) support arm section 22. The articulate arm assembly 18 is supported by an upright support shaft 24. The support shaft 24 is movably mounted on the console 16 for extension and retraction in elevation. The first support arm section 20 is movably coupled to the upright support shaft 24 by a bearing assembly 26 which permits rotational movement of the first support arm section 20 relative to the support shaft 24. Likewise, the second support arm section 22 is rotatably coupled to the first support arm section 20 by a bearing assembly 28. According to this arrangement, the proximal and distal support arm sections 20, 22 are rotatably coupled together for folding movement relative to each other.

The angular position of the first support arm section 20 relative to the second support arm section 22 is selectively locked and released by a band brake assembly 30 as shown in FIG. 9 and FIG. 10. The band brake assembly 30 includes a pair of friction bands 32, 34 fitted about a coupling sleeve 44 and movable from a released, non-engaging position as shown in FIG. 9 to a locked, brake position in response to retraction of the friction bands 32, 34. The friction bands 32, 34 are selectively retracted by lever arms 36, 38 which are mounted for pivotal movement on a pin 40. One end 36A of the lever arm 36 is connected to the free end 32A of the friction band 32, and the opposite end 36B of the lever arm is attached to the plunger 42 of an electrical solenoid K1. According to this arrangement, when the solenoid K1 is energized, the plunger 42 retracts and draws the lever arm 36 in a clockwise movement. As this occurs, the coil spring 46 is compressed, thereby releasing the friction band 32 from engagement against the external cylindrical surface of the coupling sleeve 44. When operating power is removed from the solenoid K1, the coil spring 46 pushes the lever arm end portion 36B in counterclockwise movement, thereby drawing the friction bands 32, 34 into engagement with the coupling sleeve 44. When power is removed from the solenoids, the second support arm section 22 is locked relative to the first support arm section 20.

The second friction band 34 is operated by a second solenoid K2 which is mounted on the opposite side of the support arm 20, as shown in FIG. 2. The plunger of the second solenoid K2 is connected to the lever arm 38 and is mounted for pivotal movement on the pin 40. The solenoids K1, K2 are electrically coupled in parallel to a source of electrical operating power through a position controller 46 as shown in the electrical circuit diagram of FIG. 11.

The bearing assembly 28 includes a cylindrical thrust bearing 48 which is connected to the first support arm section 20 by a bracket 50. The second support arm section 22 is attached to the cylindrical coupling sleeve 44 which receives the cylindrical thrust bearing 48 in telescoping engagement. The friction band 32 is engagable against the coupling cylindrical coupling sleeve 44. As shown in FIG. 10, the second friction band 32 is fitted about the coupling sleeve 44 and is actuated by the second solenoid K2. The thrust bearing 48 is attached to the first support arm section 20 by a coupling sleeve 52, an annular collar 48A, and the bracket 50. The coupling sleeve 52A is stabilized against the coupling sleeve 44 by an annular collar 54.

The first support arm section 20 is rotatably coupled to the upright support shaft 24 by the bearing assembly 26. The bearing assembly 26 has substantially the same construction as the bearing assembly 28, with the distal end of the upright support post 24 being engaged by a pair of friction bands (not illustrated) which are attached to lever arms and solenoids K3, K4 for selectively locking and releasing the angular position of the first support arm section 20 with respect to the upright support arm 24. The solenoids K3, K4 are electrically wired in parallel with the solenoids K1, K2 for receiving operating power through the position controller 46 as shown in FIG. 11.

Figure 4:
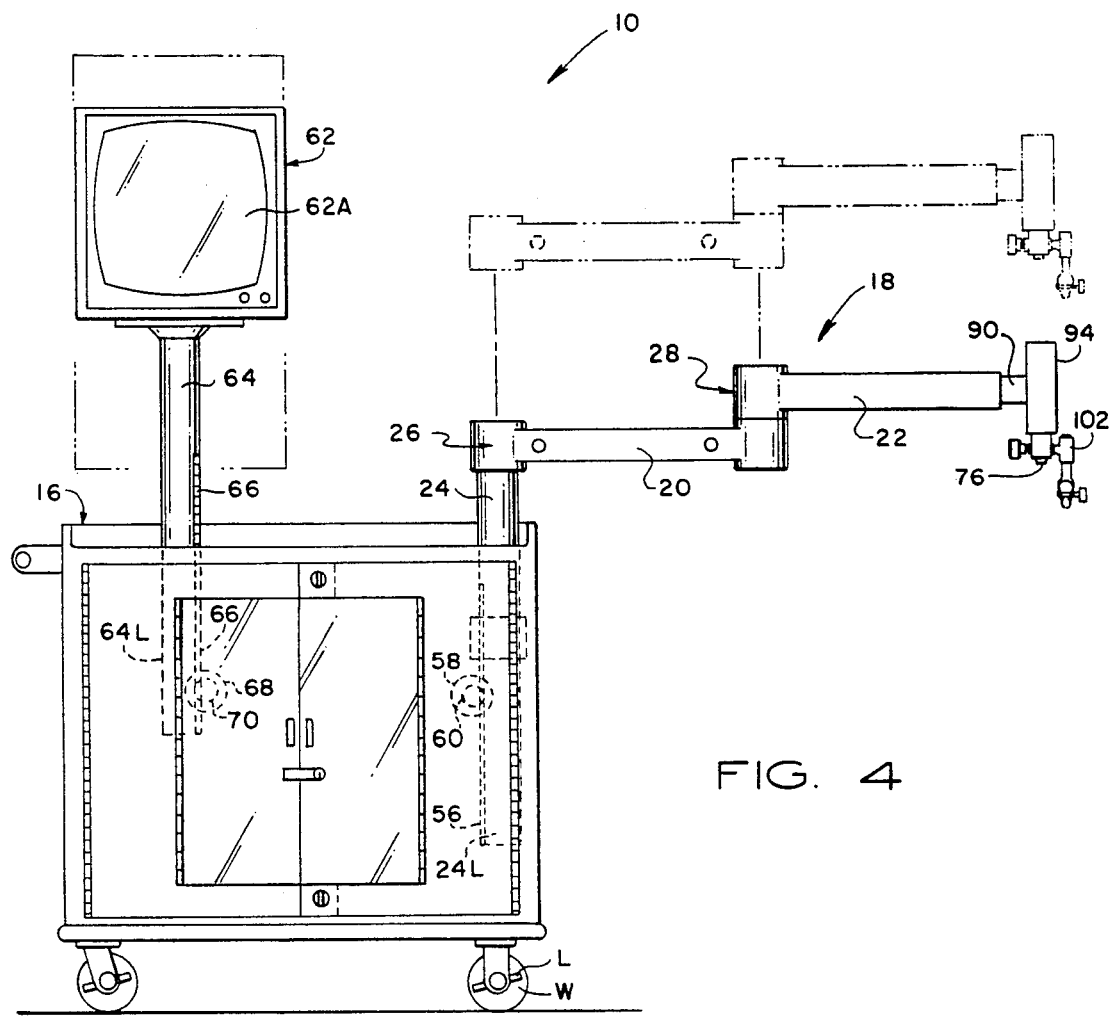
FIG. 4 is a front elevational view of the positioning apparatus shown in FIG. 1.
Figure 5:
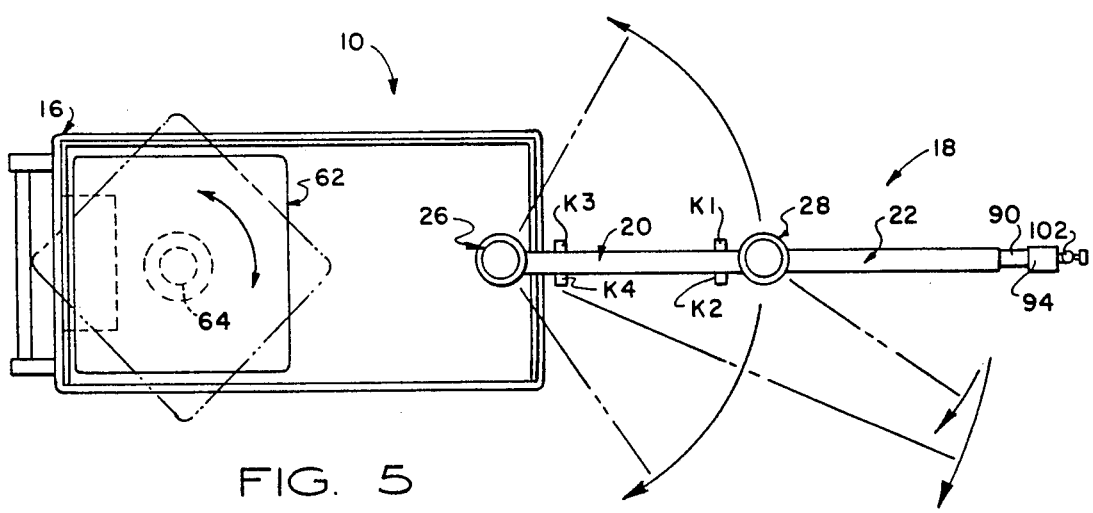
FIG. 5 is a top plan view thereof.
Figure 11:
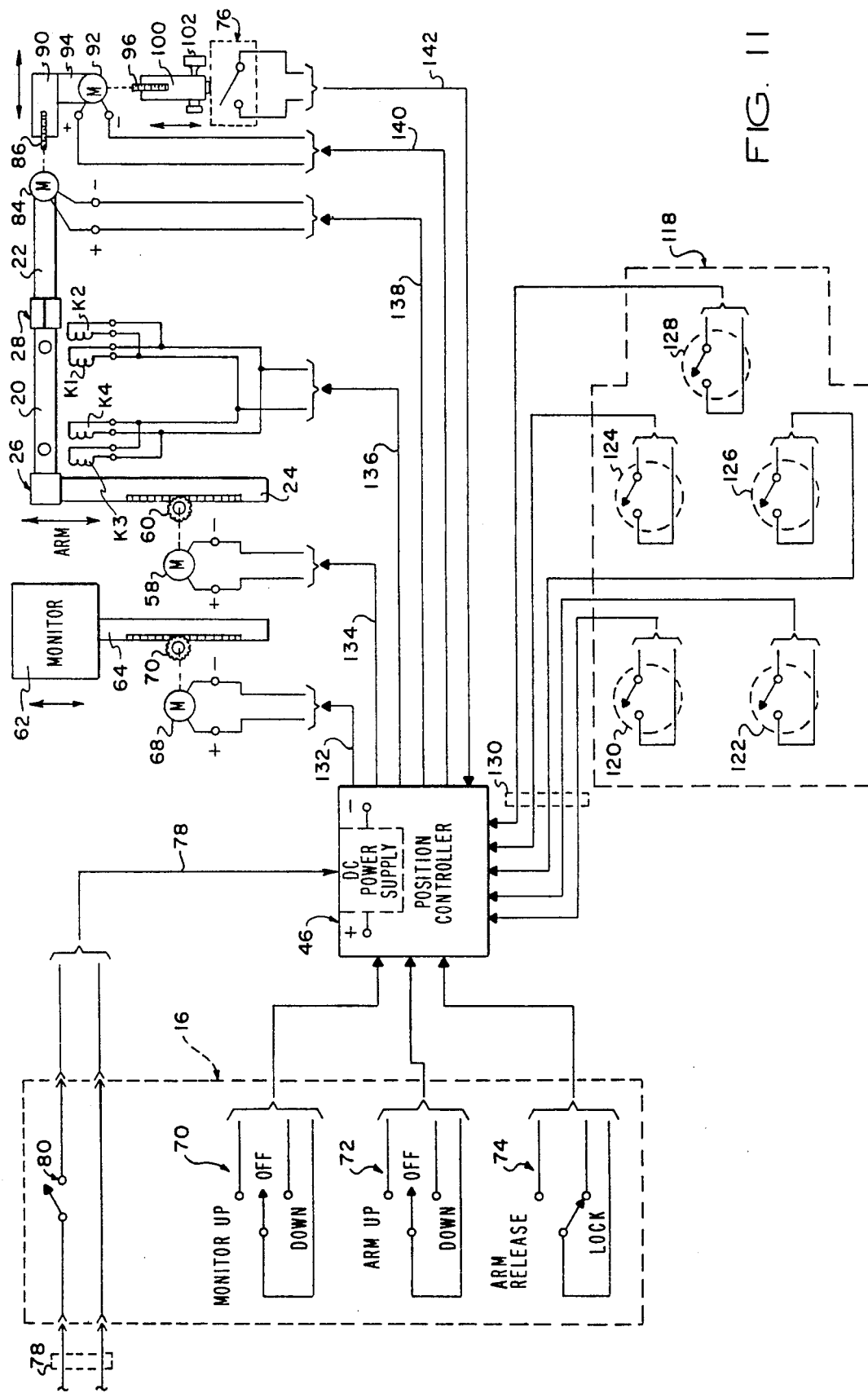
FIG. 11 is a simplified control circuit diagram.

As shown in FIG. 4 and FIG. 11, the upright support arm 24 has a lower end portion 24L extending into the cabinet space of the console 16, and has a toothed rack 56 formed along its external surface. A drive motor 58 is coupled to the rack 56 by a pinion gear 60. The drive motor 58 is a reversible DC motor which is capable of driving the pinion gear 60 clockwise and counterclockwise, thereby extending and retracting the upright support shaft 24. When the drive motor 58 is de-energized, the pinion 60 holds the support shaft 24 at a fixed elevation.

In the preferred embodiment of the present invention, a video display monitor 62 is supported on the console 16 by an upright shaft 64. The lower end 64L of the shaft 64 projects into the cabinet space of the console 16 and has a toothed rack 66 formed along its external surface. The video monitor 62 is lifted and lowered in elevation by a drive motor 68 which is coupled in driving relation with the rack 66 by a pinion gear 70. The video display monitor 62 is pivotally attached to the upright shaft 64 so that its viewing screen 62A can be turned and aligned with the surgeon's field of view. The video display monitor 62 is elevated above the articulated arm assembly 18 so that the surgeon's view will not be obscured.

Referring again to FIG. 3 and FIG. 11, elevation control of the video monitor 62 and coarse control of instrument elevation is provided by the drive motors 58, 68 by actuation of switches 70, 72 which are console mounted and operable by an attendant. The switches 70, 72 are single-pole, double-throw switches and are operable in a momentary ON mode when depressed, and automatically turned OFF when released. Release and lock operation of the solenoids K1, K2, K3 and K4 is provided by a console mounted, single-pole, single-throw switch 74 which operates in the ON mode when depressed, and which automatically turns OFF when released. The solenoids are also operable through a manual override switch 76 which is mounted on the articulated arm assembly 18 as discussed below.

When the console 16 is set up and locked in position as shown in FIG. 1, an attendant connects the power service cable 78 to an AC power outlet and makes AC power available to the controller 46 within the console unit by turning on the master switch 80. A DC power supply within the controller 46 provides the DC operating current for the drive motors and solenoids. The control switch 72 is then depressed to drive the articulated arm assembly 18 upwardly until an appropriate clearance elevation has been reached. The solenoids K1, K2, K3 and K4 are then released by depressing control switch 74 and the articulated arm sections 20, 22 are manually extended over the operating table. After the approximate position has been established, the control switch 74 is released and the solenoids are de-energized, thereby locking the angular position of the arms 20, 22. The video monitor 62 is elevated to an appropriate viewing elevation, and the viewing screen 62A is rotated in alignment with the surgeon's field of view. After the instrument 14 has been attached to the end of the articulated arm, it is covered by a sterile drape 82.

Referring to FIG. 7 and FIG. 8, fine adjustment of instrument position across the surgical site along longitudinal axis C is provided by a DC drive motor 84. The stator of the DC drive motor 84 is mounted in a fixed position on the second support arm section 22, and has a rotatable screw shaft 86 received in threaded engagement with a threaded coupling collar 88 which is attached to a first extension arm 90. The first extension arm 90 is received in telescoping engagement within the bore of the support arm 22. Upon clockwise and counterclockwise rotation of the rotor screw shaft 86, the first extension arm 90 is extended and retracted along the longitudinal axis C of the second support arm section 22.

Fine adjustment of the endoscope instrument along transverse axis D is provided by a reversible DC drive motor 92. The drive motor 92 is mounted within a tubular housing 94 which is oriented at a right angle with respect to the longitudinal axis C of the first extension arm 90. The drive motor 92 has a rotor screw shaft 96 which is received in threaded engagement with a coupling collar 98. The coupling collar 98 is secured to the end of a second extension arm 100 which is slidably received in telescoping engagement within the bore of the tubular housing 94. Upon clockwise and counterclockwise rotation of the threaded rotor shaft 96, the second extension arm 100 is extended and retracted along the longitudinal axis D of the housing 94.

Referring again to FIG. 3, FIG. 7 and FIG. 8, the endoscope instrument 14 is secured to the extension arm 100 by a rotatable coupler 102. The coupler 102 is secured for rotation on the distal end of the extension arm 100 by a screw clamp 104. The screw clamp 104 includes a threaded shaft 106 and a coupling collar 108. When the screw clamp 104 is released, the coupler 102 is rotatable with respect to the longitudinal axis E of the threaded shaft 106.

The endoscope instrument 14 is a fiber optic endoscope which has an insertion probe section 14A and a fiber optic video camera 110. The fiber optic video camera is connected by a signal cable 112 to a video recorder unit 114 inside the cabinet space of the console 16. A light source is incorporated in the probe section 14A of the endoscope, whereby an image of the internal cavity is provided on the video monitor screen 62A. The probe section 14A of the endoscope is secured by a screw clamp 116. The insertion orientation of the endoscope instrument 14 is adjustable by releasing the screw clamp 104 and rotating the coupling collar 104 until the appropriate orientation is presented on the viewing screen 62A.

According to this arrangement, the surgeon observes the video presentation and makes fine adjustments of the fiber optic camera orientation by selectively actuating the drive motors 84, 92 after the initial insertion orientation has been established. According to an important feature of the invention, selective actuation of the reversible drive motors 84, 92 is provided by a pressure responsive foot switch assembly 118. The foot switch assembly 118 includes longitudinal extend and retract foot switches 120, 122 and up and down pressure responsive foot switches 124, 126. A master control foot switch 128 is also provided.

The foot switches 120, 122, 124 and 126 are momentary ON switches which automatically turn OFF in the absence of pressure. The master control switch 128 is a single-pole, single-throw momentary ON switch which is electrically coupled to an enable circuit within the position controller 46. The enable circuit locks up four control relay switches which are coupled in series with the foot switches 120, 122, 124 and 126. Actuation of the master control foot switch 128 sets the enable circuit, thereby rendering each foot switch active. A second actuation of the foot switch causes the enable circuit to reset, thereby automatically disabling each of the foot switches 120, 122, 124 and 126.

If fine adjustment of elevation or longitudinal position is desired during the course of a surgical procedure, the operating surgeon S applies momentary foot pressure to the master control switch 128 which enables the foot switches 120, 122, 124 and 126. The surgeon S then applies foot pressure to the appropriate switch until the desired video presentation is obtained. After the desired video presentation is obtained, momentary foot pressure is again applied to the enable switch 128 which disables the fine control switches and prevents inadvertent adjustment.

The foot switches 120, 122, 124 and 126 and the master control switch 128 are electrically coupled to the position controller 46 by a multiple conductor cable 130. The position controller 46 applies DC operating voltage of the appropriate polarity to the drive motors 84, 92 in response to actuation of the foot switches 120, 122, 124 and 126.

The position controller 46 also applies DC operating voltage of the appropriate polarity to the arm and monitor drive motors 58, 68 in response to actuation of the console mounted position switches 70, 72. The solenoids are energized and the band brakes are released by actuation of the console mounted arm release switch 74, or the articulated arm mounted, manual override switch 76. Preferably, the internal DC power supply within the position controller 46 produces 12 volts DC which is applied in the appropriate polarity to the monitor drive motor 68 on a two pair conductor cable 132. Likewise, DC operating voltage of the appropriate polarity is applied to the articulated arm drive motor 58 on a two pair conductor cable 134. The parallel connected solenoids K1, K2, K3 and K4 are likewise energized by 12 volts DC through a two pair conductor cable 136.

The fine control drive motors 84, 92 are energized with the appropriate operating voltage polarity by two pair conductor cables 138, 140, respectively. The manual override switch 76 which is attached to the underside of the extension arm 100 is coupled to the position controller 46 by a two pair conductor cable 142. This switch and wiring arrangement permits an attendant standing at the end of the console 16 to exercise coarse control of monitor elevation and articulated arm elevation during initial setup. It also permits the surgeon S to exercise coarse position control of the articulated arm assembly, and hands free, fine control of instrument elevation and extension by applying foot pressure to selected foot switches 120, 122, 124, 126 and 128.

Referring again to FIG. 1 and FIG. 3, the console 16 is positioned on one side of the operating table, and the foot switch assembly 118 is positioned on the opposite side, adjacent to the operating table support pedestal 144. This orientation of the console 16 provides access to the surgical site for an attendant, without blocking the surgeon's view of the monitor screen 62A. The switches 120, 122, 124, 126 and 128 are known and referred to in the art as "pancake" switches, and are sandwiched between two sheets of flexible rubber material. The multiple conductor switch cable 130 is coupled to the position controller by a multiple pin connector which can be plugged in and disconnected as desired.

Figure 3:
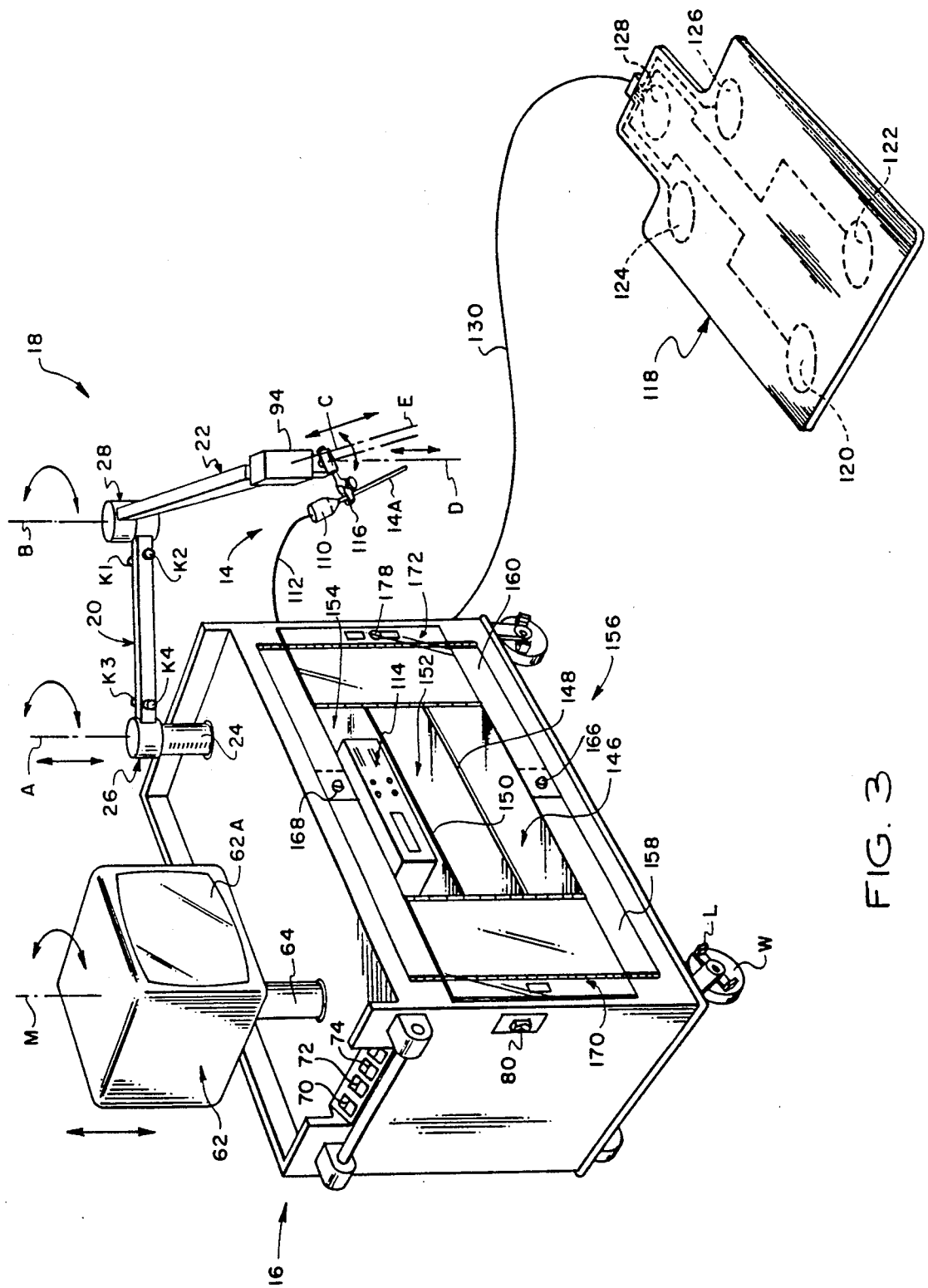
FIG. 3 is a perspective view of the portable console positioning apparatus of FIG. 1 with the surgical operating table removed.

Consequently, the foot switch assembly 118 can be folded or rolled up and stored within the lower storage space 146 within the console 16. The storage space of the console 16 is partitioned by two divider panels 148, 150 providing separate storage compartments 152, 154. As shown in FIG. 3, the video recorder 114 is received within the upper storage compartment 154, and is supported by the upper partition panel 150. The next lower storage compartment 152 is adapted for storage of accessories such as a video camera, endoscope equipment and video interconnect equipment. The lower storage compartment 146 is adapted to receive the electrical power cable, the foot switch assembly 118 and the foot switch connecting cable 130.

The storage compartments are secured by a dual door assembly 156. The dual door assembly 156 includes first and second metal panels 158, 160 which are connected by hinges 162, 164 to the front frame of the console 16. The panels 158, 160 have overlapping end portions which are secured together by quarter turn screw fasteners 166, 168.

The contents of the storage compartments are made visible through double glass doors 170, 172. The glass doors 170, 172 are received within rectangular cutout windows Within the metal doors 158, 160. The glass doors 170, 172 are mounted on the metal doors by hinges 174, 176. The glass doors are secured together by a key lock 178. In addition to revealing the equipment stored within the internal console compartments, the glass doors also permit wireless communication, for example, FM or infrared signalling, between a handheld controller and the video control unit 114 when the glass doors are closed. The primary purpose of the double glass doors 170, 172 is to permit quick and easy access to the accessories which are stored within the internal compartments of the console 16. The larger metal doors 158, 160 are opened only when it is necessary to perform maintenance or repairs.

In addition to providing a stable platform for the endoscope instrument 14, the console 16 provides stable support for the video monitor 62. The video monitor 62 is mounted for rotation on the upright support shaft 64, and is rotatable clockwise and counterclockwise with respect to the longitudinal axis M for alignment with the field of view of the operating surgeon S. The video monitor 62 is electrically connected to the video control unit 114 for providing a real time display of the internal images produced by the video camera 110. Additional viewing monitors may be coupled to the monitor 62 and to the Video control unit 114 for observation by attendants.

Fine positioning control of the endoscope instrument 14 can be accomplished quickly and easily by actuating the appropriate switches on the foot switch assembly 118. The articulated arm assembly 18 can be readjusted as desired by the surgeon by actuating the manual override switch 76. Otherwise, the positioning control is carried out entirely by foot movements, thereby freeing the surgeon's hands for manipulating other surgical instruments, for example, a grasper, hook, spatula, forceps and dissector, as indicated in FIG. 1.

Because the arm assembly 18 is articulated, it permits the console 16 to be set up away from the operating table, out of the sterile field. Because of the stable support provided by the console 16, no additional support equipment is required. The surgical instrument support apparatus 10 is easy to set up by one person and requires only minimal training. No additional support personnel are required for holding or stabilizing the endoscope 14. Because of the range of the articulated arm assembly 18, the console 16 can be oriented away from the operating table, thereby providing access to the surgical site on the near side of the operating table. The sterile drape 82 completely covers the articulated arm and permits the surgeon S to operate freely without contaminating the sterile field. The manual override switch 76 is covered by the sterile drape 82 and is actuated by finger pressure applied through the drape.

Referring again to FIG. 7 and FIG. 8, the clamp 116 is sterile and preferably disposable. The clamp 116 is inserted through a preformed opening in the sterile drape 82. The clamp 116 has a shaft portion 116A which is coupled to the collar 108 by a bayonet/detent coupling. The clamp 116 is freely rotatable about its longitudinal axis F. Additionally, the collar 108 is freely rotatable about the longitudinal axis E of the screw clamp 104. The clamp 116 is adjustable, thereby accommodating a wide range of endoscope sizes/diameters.

Upon completion of a procedure, the articulated arm assembly 18 is retracted, released and folded inwardly, and the monitor 62 is retracted as shown in FIG. 6. The accessories, including the foot switch assembly 118 and signal cable 130, are stored within the console compartments, a nd the glass doors 170, 172 are locked. The portable console assembly 10 is then ready for storage out of the operating area, and can be moved from one operating room to another.

Although the invention has been described with reference to a preferred embodiment, and with reference to a laparoscope instrument, the foregoing description is not intended to be construed in a limiting sense. Various modifications of the disclosed embodiment as well as alternative applications of the invention in other procedures will be suggested to persons skilled in the art by the foregoing specification and illustrations. It is therefore contemplated that the appended claims will cover all such modifications, applications and embodiments as fall within the true scope of the invention.

What is claimed is:

1. Freestanding surgical instrument support apparatus for use adjacent to a surgical operating table comprising, in combination:

a portable console having wheels for permitting rolling movement of the console from one station to another;

an upright support shaft movably mounted on said console for extension and retraction in elevation relative to said console;

a support arm coupled to the upright support shaft for rotation about the longitudinal axis of the upright support shaft;

a first extension arm movably mounted on said support arm for extension and retraction along the longitudinal axis of said support arm;

a second extension arm movably mounted on said first extension arm for extension and retraction along an axis transverse with respect to the longitudinal axis of said first extension arm;

an instrument coupler movably mounted on said second extension arm for rotation about a fourth axis transverse with respect to the longitudinal axis of said second extension arm;

electromechanical control means coupled to said upright support shaft, said support arm and said extension arms for controlling the rotational position of the support arm and the extension and retraction of the first and second extension arms; and, a floor switch control circuit coupled to said electromechanical control means for controlling the extension and retraction of said instrument coupler along the longitudinal axis of said support arm, and for controlling the extension and retraction of said instrument coupler in elevation with respect to support arm, said floor switch control circuit having electrical switches which may be actuated by foot pressure applied by a surgeon while said surgeon is performing a surgical procedure on a patient lying on the operating table.

2. Freestanding surgical instrument support apparatus for use adjacent to a surgical operating table comprising, in combination:

a portable console having wheels for permitting rolling movement of the console from a storage location to an operating table location;

an upright support shaft movably mounted on said console for extension and retraction in elevation relative to said console;

a support arm movably coupled to the upright support shaft for rotation about the longitudinal axis of the upright support shaft;

lock apparatus mounted on said support arm and releasably coupled to the upright support shaft for selectively locking the support arm in a fixed position on the upright support shaft and selectively releasing the support arm for rotational movement about the longitudinal axis of the upright support shaft;

a second support arm movably mounted on the first support arm for extension and retraction along the longitudinal axis of the first support arm;

a first drive motor mounted on the first support arm, said first drive motor having a rotor shaft movably coupled to said second support arm for extending and retracting the second support arm along the longitudinal axis of the first support arm;

a third support arm movably mounted on the second support arm for extension and retraction along an axis transverse with respect to the longitudinal axis of the second support arm;

a second drive motor mounted on the second support arm, said second drive motor having a rotor shaft movably coupled to the third support arm for driving it in extension and retraction along said transverse axis;

first (up), second (down), third and (extend) and fourth (retract) pressure responsive on/off switches electrically coupled to the first and second drive motors for selectively energizing each drive motor in a forward rotation operating mode and a reverse rotation operating mode, whereby the longitudinal position of the second support arm can be adjusted by selectively actuating the extend and retract switches, and whereby the elevation of the third support arm can be adjusted by selectively actuating the up and down pressure responsive switches; and, said pressure responsive on/off switches being adapted for floor installation adjacent to an operating table whereby said switches can be actuated by foot pressure applied by a surgeon during the course of a surgical procedure being performed by said surgeon on a patient lying on the operating table.

3. A portable console assembly for selectively positioning and stabilizing an endoscope instrument during a surgical procedure comprising, in combination:

a portable console having side panels enclosing an internal storage compartment;

a video monitor mounted on said console for extension and retraction in elevation;

a support arm coupled to said console for extension and retraction in elevation;

a video processor supported on said console, said video processor having an input adapted for electrical connection to an endoscope instrument and having an output coupled to said video monitor;

a first extension arm movably mounted on said support arm for extension and retraction along the longitudinal axis of said support arm;

a first drive motor mounted on said support arm, said first drive motor having a rotor shaft movably coupled to said first extension arm for extending and retracted the first extension arm along the longitudinal axis of said support arm;

a second extension arm movably mounted on the first extension arm for extension and retraction along an axis transverse with respect to the longitudinal axis of the first extension arm;

a second drive motor mounted on the first extension arm, said second drive motor having a rotor shaft movably coupled to the second extension arm for driving it in extension and retraction along said transverse axis; and, on/off switches electrically coupled to the first and second drive motors for selectively energizing each drive motor in a forward rotation operating mode and a reverse rotation operating mode.

4. A portable console assembly as defined in claim 3, wherein said support arm includes a first support arm section and a second support arm section pivotally mounted on the first support arm section for rotation; and, brake apparatus mounted on said first support arm section and releasably coupled to the second support arm section for selectively locking the first and second support arm sections in a fixed angular position and for selectively releasing the second support arm section for rotational movement relatives to the first support arm section.

5. A portable console assembly as defined in claim 3, including:

an upright support shaft movably mounted on said console for extension and retraction in elevation relative to said console, said video monitor being mounted on said upright support shaft; and, a drive motor mounted on said console, said drive motor having a rotor coupled to said upright support shaft for extending and retracting said upright support shaft and video monitor in response to clockwise and counterclockwise rotation of said rotor shaft.

6. A portable console assembly as defined in claim 3, including:

an upright support shaft movably mounted on said console for extension and retraction in elevation relative to said console, said support arm being coupled to said upright support shaft; and, a drive motor mechanically coupled to said upright support shaft for extending and retracting said upright support shaft and support arm in elevation in response to forward and reverse operation of said drive motor.

7. A portable console assembly as defined in claim 3, including an upright support shaft movably coupled to said console and an electromechanical brake connected between the upright support shaft and said support arm, and including a release switch electrically coupled to said electromechanical brake for selectively locking and releasing said support arm with respect to said upright support shaft.

8. A portable console assembly as defined in claim 3, wherein said console has a rectangular frame opening providing access to said internal storage compartment area, including first and second primary door panels pivotally connected by hinges to said console frame, said first and second primary door panels having first and second rectangular window openings, respectively, and having first and second transparent door panels overlying the window openings and pivotally connected by hinges to said first and second primary door panels, respectively, said first and second transparent door panels being operable independently of said first and second primary door panels for providing access to said console storage compartment space.

9. Surgical instrument support apparatus comprising, in combination:

a portable console having a universal positioning arm for holding a surgical instrument during a surgical procedure;

said universal positioning arm including proximal and distal support arm sections which are rotatably coupled together for folding movement relative to each other;

a clamp coupled to the distal support arm section for holding a surgical instrument;

a first reversible driver motor interposed between the clamp and the distal support arm section for extending and retracting the clamp along an axis substantially in parallel with the longitudinal axis of the distal support arm section;

a second reversible drive motor coupled between the distal support arm section and the clamp for extending and retracting the clamp along an axis which is transverse to the longitudinal axis of the distal support arm section; and, a floor switch control circuit coupled to the reversible drive motors for operating the first and second reversible drive motors in forward and reverse rotation for producing extension and retraction of the clamp along the longitudinal axis of the positioning distal support arm section, and for producing extension and retraction of the clamp along said transverse axis, respectively.

10. Surgical instrument support apparatus for use in conjunction with a surgical operating table comprising, in combination:

a portable console;

an articulated support arm movably mounted in elevation on said console, said articulated support arm having a proximal support arm section and a distal support arm section;

a video display monitor having a viewing screen movably mounted in elevation on said console;

means coupled to said console and said articulated support arm for producing coarse position control of the elevation of said articulated support arm relative to said console;

a clamp coupled to the distal support arm section of said articulated support arm for holding a surgical instrument;

means coupled between the distal support arm section and said clamp for exercising fine position control of the extension and retraction of a surgical instrument held by said clamp along the longitudinal axis of said distal support arm section;

means coupled between the distal support arm section and said clamp for exercising fine position control of the elevation of said clamp and a surgical instrument held by said clamp relative to the elevation of said articulated support arm; and, a floor switch control circuit coupled to said position control means for controlling the extension and retraction of the clamp along the longitudinal axis of the distal support arm section, and for controlling the extension and retraction of the clamp in elevation with respect to the articulated support arm, said floor switch control circuit having electrical switches which may be actuated by foot pressure applied by a surgeon while observing said viewing screen.

* * * * *

UNITED STATES PATENT AND TRADEMARK OFFICE
CERTIFICATE OF CORRECTION

PATENT NO. : 5,184,601

DATED : 02/09/93

INVENTOR(S) : John M. Putman

It is certified that error appears in the above-identified patent and that said Letters Patent is hereby corrected as shown below:

Column 10, line 2, "Within" should be -- within --.

Column 10, line 27, "Video" should be -- video --.

Column 11, line 3, "a nd" should be -- and --.

Column 12, line 28, the word "and" should be deleted before the word "(extend)".

Column 13, lines 24, 25, "relatives" should be "relative".

Column 14, line 14, "driver" should be "drive".

Signed and Sealed this

Twenty-sixth Day of April, 1994

Attest:

BRUCE LEHMAN

*Attesting Officer*     Commissioner of Patents and Trademarks